US00PP33723P2

(12) United States Plant Patent
Vitten et al.

(10) Patent No.: US PP33,723 P2
(45) Date of Patent: Dec. 7, 2021

(54) RASPBERRY PLANT NAMED 'DRISRASPEIGHTEEN'

(50) Latin Name: ***Rubus idaeus* L.**
Varietal Denomination: DrisRaspEighteen

(71) Applicant: Driscoll's, Inc., Watsonville, CA (US)

(72) Inventors: Matthias D. Vitten, Watsonville, CA (US); Lluvia V. Gutierrez, Watsonville, CA (US); Kyle Rak, Watsonville, CA (US); Luis Miguel Rodriguez, Watsonville, CA (US); James Heilig, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/003,817

(22) Filed: Aug. 26, 2020

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP7,528 | P | 5/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| PP27,644 | P3 | 2/2017 | Hamilton et al. |
| PP28,775 | P2 | 12/2017 | Hamilton et al. |
| PP28,856 | P3 | 1/2018 | Vitten et al. |
| PP29,402 | P2 | 6/2018 | Vitten et al. |
| PP30,577 | P2 | 6/2019 | Vitten et al. |
| PP30,733 | P2 | 7/2019 | Hamilton et al. |
| PP31,850 | P2 | 6/2020 | Hamilton et al. |

OTHER PUBLICATIONS

Cousineau et al., "Use of Isoenzyme Analysis to Characterize Raspberry Cultivars and Detect Cultivar Mislabeling", HortScience vol. 27, No. 9, Sep. 1992, pp. 1023-1025.
Harrison et al., Unpublished U.S. Appl. No. 17/003,824, filed Aug. 26, 2020, titled "Raspberry Plant Variety Named 'DrisRaspNineteen'".
Vitten et al., Unpublished U.S. Appl. No. 16/602,687, filed Nov. 19, 2019, titled "Raspberry Plant Variety Named 'DrisRaspSeventeen'".
Vitten et al., Unpublished U.S. Appl. No. 16/501,853, filed Jun. 19, 2019, titled "Raspberry Plant Named 'DrisRaspFifteen'".
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Anne Marie Grunberg
(74) *Attorney, Agent, or Firm* — Morrison & Foerster LLP

(57) ABSTRACT

A new and distinct variety of raspberry plant named 'DrisRaspEighteen', particularly selected for its yield potential and flavor, is disclosed.

4 Drawing Sheets

Latin name:
Botanical classification: *Rubus idaeus* L.
Varietal denomination: The varietal denomination of the claimed variety of raspberry plant is 'DrisRaspEighteen'.

BACKGROUND OF THE INVENTION

Raspberries are the edible fruit of a multitude of plant species in the genus *Rubus* of the rose family. Most raspberry species are in the subgenus *Idaeobatus*. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L.), which has been denominated as 'DrisRaspEighteen'.

Raspberry plant variety 'DrisRaspEighteen' was discovered in Santa Cruz County, Calif. in July of 2015 and originated from a cross between the female parent 'DrisRaspTwelve' (U.S. Plant Pat. No. 30,577) and the male parent 'OrisRaspThirteen' (U.S. Plant Pat. No. 29,402). The original seedling of the new variety was first asexually propagated in Santa Cruz County, Calif. via root cuttings in October 2015.

'DrisRaspEighteen' was subsequently asexually propagated via root cuttings, and has undergone testing in Santa Cruz County, Calif. for five years (2014 to 2019). The present variety has been found to be stable and reproduce true to type through successive asexual propagations via root cuttings and tissue culture.

'DrisRaspEighteen' was particularly selected for its yield potential and flavor.

BRIEF DESCRIPTION OF THE DRAWINGS

This new raspberry plant is illustrated by the accompanying photographs. The colors shown are as true as can be reasonably obtained by conventional photographic procedures. The photographs are of plants that are two years old.

DETAILED BOTANICAL DESCRIPTION

Figure 1:
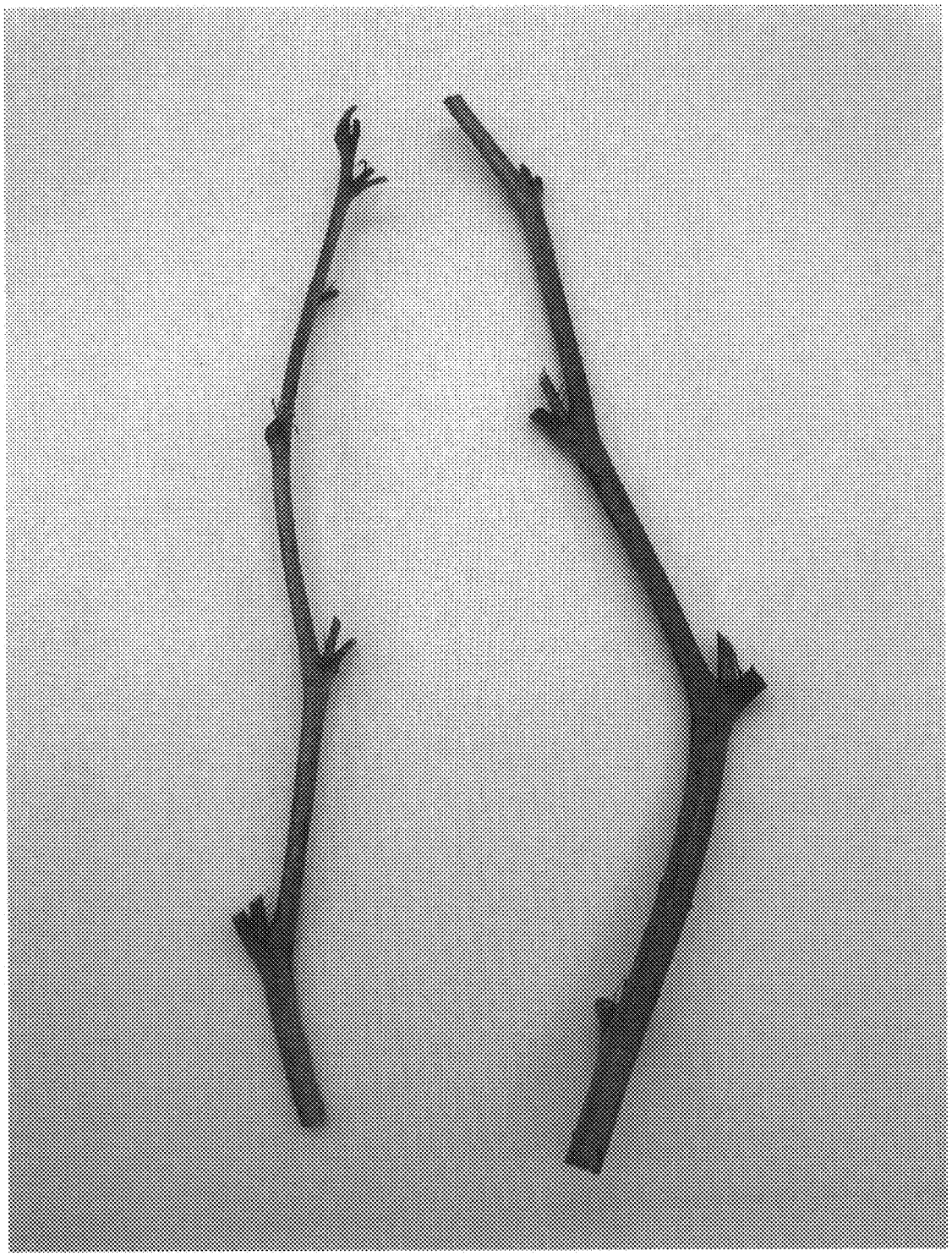
FIG. 1 illustrates sections of canes of raspberry variety 'DrisRaspEighteen'.
Figure 2:
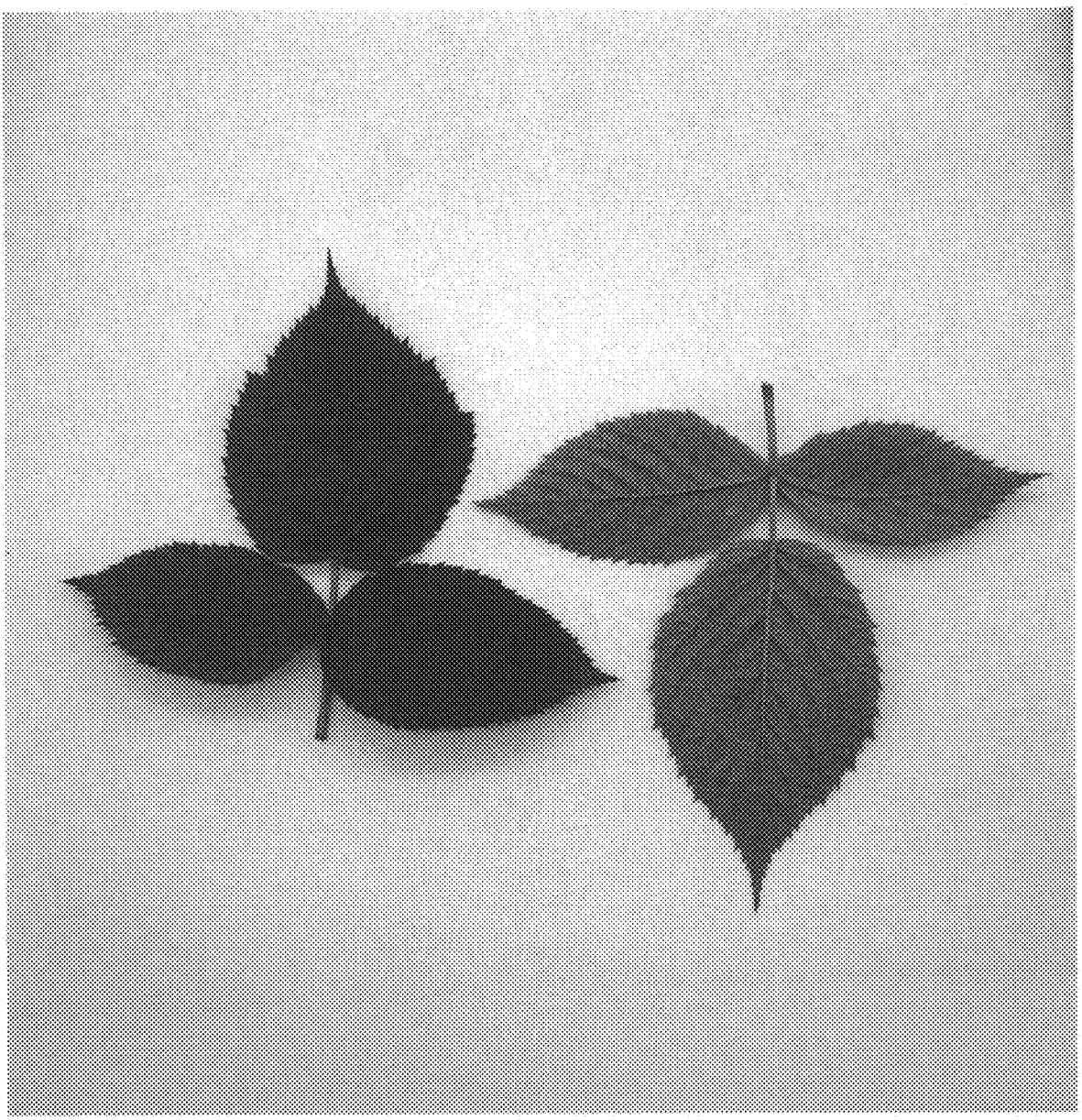
FIG. 2 illustrates the upper surface (left leaf) and the lower surface (right leaf) of leaves of raspberry variety 'DrisRaspEighteen'.
Figure 3:
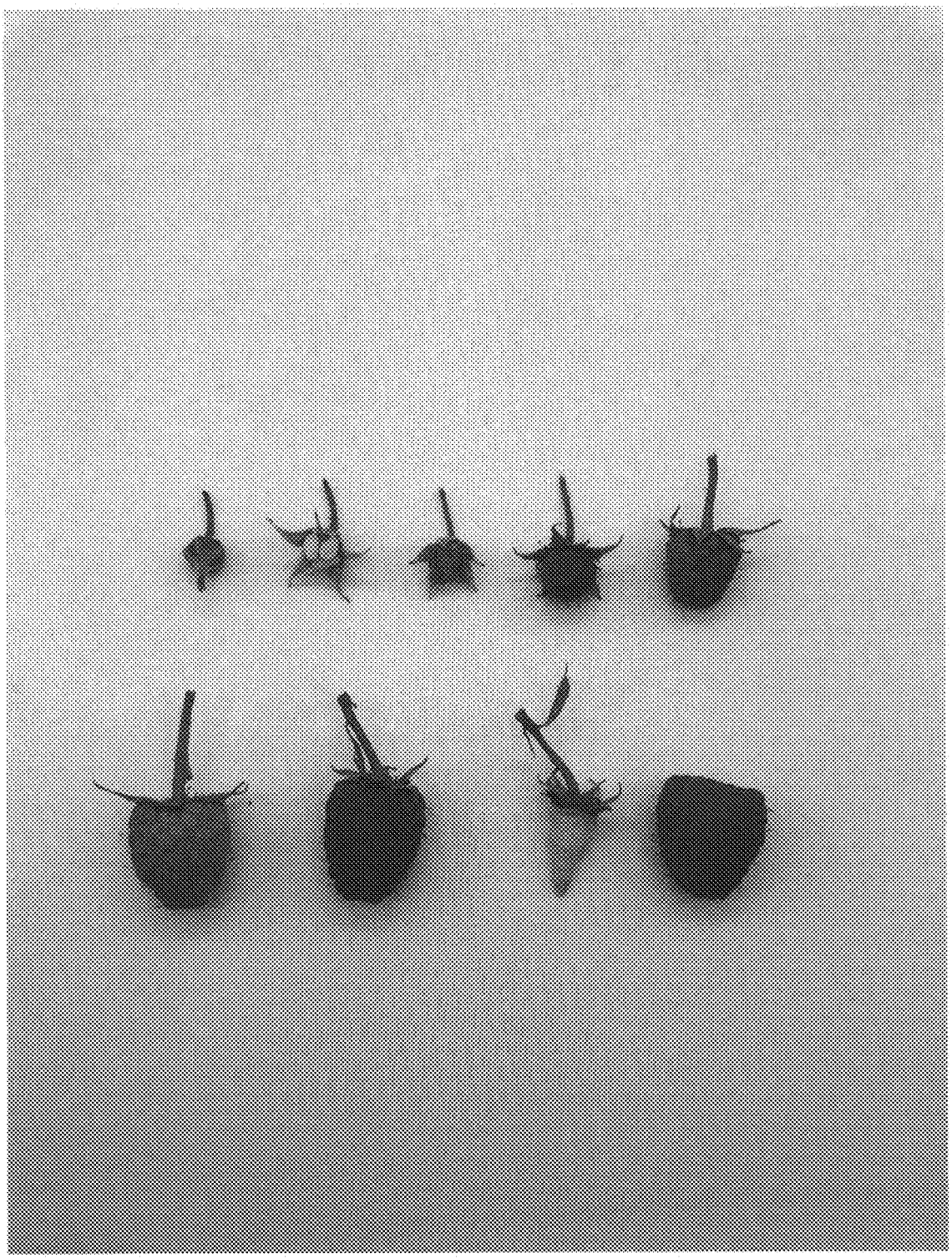
FIG. 3 illustrates flowers and fruit of raspberry variety 'DrisRaspEighteen' at various stages of development.
Figure 4:
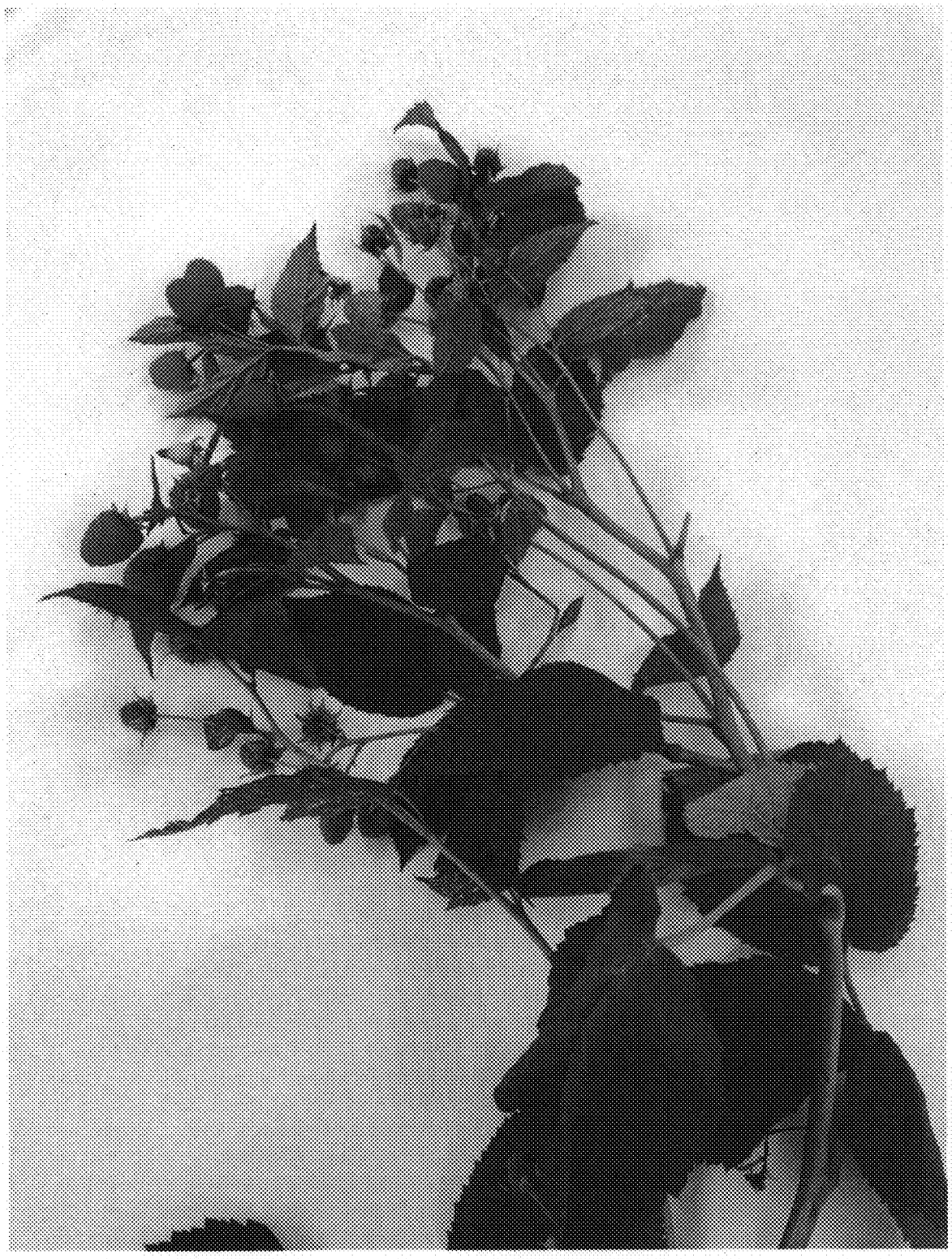
FIG. 4 illustrates a section of a plant of raspberry variety 'DrisRaspEighteen'.

The following descriptions set forth the distinctive characteristics of 'DrisRaspEighteen'. Unless where otherwise noted, the data that define these characteristics are based on observations taken from 'DrisRaspEighteen' plants that were two years old, grown in Santa Cruz County, Calif. from 2014 to 2019. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspEighteen' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family.*—Rosaceae.

*Botanical.*—*Rubus idaeus* L.

*Common name.*—Raspberry.

*Variety name.*—'DrisRaspEigiateen'.

Parentage:

*Female parent.*—'DrisRaspTwelve' (U.S. Plant Pat. No. 30,577).

*Male parent.*—'DrisRaspThirteen' (U.S. Plant Pat. No. 29,402).

Plant:

*Height.*—173.0 cm.

*Width.*—129.5 cm.

*Length/width ratio.*—1.3.

*Growth habit.*—Semi-upright.

*Primocane* (*current year's cane*).—Color: RHS N144D (Strong yellow-green). Cane length in autumn: 194 cm. Internodal distance at central ⅓ of cane: 7.28 cm. Anthocyanin coloration of cane: Absent or very weak. Cane bloom: Absent or very weak. Vegetative bud length (at central ⅓ of cane): 7.37 mm.

*Very young shoot.*—Color: RHS 145A (Strong yellow-green). Anthocyanin coloration of apex during rapid growth: Absent.

*Floricane* (*previous year's cane*).—Dormant cane color: RHS 199B (Light olive brown). Fruiting lateral attitude: Semi-erect. Floricane fruiting lateral length: 93 cm.

*Prickles* (*spines*).—Presence: Present. Density: Sparse. Number of prickles on primocanes: 4-4.5 per cm$^2$. Number of prickles on floricanes: 4-4.5 per cm$^2$. Length at 1 m height at end of harvest (from base to tip): 1.31 mm. Color: RHS 59B (Deep purplish red).

Leaves:

*Predominant number of leaflets.*—Three.

*Profile of leaflets in cross section.*—Straight.

*Leaf rugosity.*—Weak.

*Color of upper* (*adaxial*) *side.*—RHS 139B (Moderate yellowish green).

*Color of lower (abaxial) side.*—RHS 139D (Moderate yellow-green).

*Terminal leaflet.*—Length: 99.4 mm. Width: 71.7 mm. Length/width ratio: 1.4.

*Lateral leaflets.*—Length: 83.7 mm. Width: 49.3 mm. Length/width ratio: 1.7. Relative position of lateral leaflets: Free.

*Rachis length between terminal leaflet and adjacent lateral leaflets.*—23.1 mm.

*Petiole.*—Length: 50.5 mm. Diameter: 2.38 mm.

Flowers:

*Diameter.*—24.53 mm.

*Petal.*—Color of upper side: RHS 155A (Pale yellow-green). Color of lower side: RHS 155A (Pale yellow-green). Length: 7.17 mm. Width: 3.86 mm. Length/width ratio: 1.9.

*Pedicel.*—Length: 47.65 mm. Diameter: 0.99 mm. Color: RHS 182A (Moderate red).

*Peduncle.*—Color: RHS 182C (Dark pink). Anthocyanin coloration: Absent.

Fruit:

*Length.*—23.08 mm.

*Diameter.*—22.17 mm.

*Length/width ratio.*—1.0.

*Length of drupelet.*—5.28 mm.

*Diameter of drupelet.*—3.80 mm.

*General shape in lateral view.*—Conical.

*Color.*—RHS 58A (Moderate purplish red).

*Glossiness.*—Strong.

*Firmness.*—Firm.

*Adherence to plug.*—Weak.

*Seed.*—Diameter: 3 mm. Shape: Lens. Color: RHS 165B (Brownish orange).

Production:

*Main bearing type.*—Both on floricane (previous year's cane) in summer and on primocane (current year's cane) in autumn.

*Primocane (current year's cane).*—Time of beginning of flowering: Early June. Time of beginning of fruit ripening: Early July. Length of fruiting period: Early July to late October. Yield: 21,370 kg to 34,007 kg of fruit per hectare per season from 7-month-old plants when grown in Watsonville, Calif.

*Floricane (previous year's cane).*—Time of vegetative bud burst: Early March. Time of beginning of flowering: Mid-April. Time of beginning of fruit ripening: Mid-May. Length of fruiting period: Early May to late July. Yield: 24,702 kg to 42,890 kg of fruit per hectare per season from 12-month-old plants when grown in Watsonville, Calif.

COMPARISONS TO PARENTAL AND REFERENCE RASPBERRY VARIETIES

'DrisRaspEighteen' differs from the female parent 'DrisRaspIwelve' (U.S. Plant Pat. No. 30,577) in that 'DrisRaspEighteen' has an improved flavor but smaller fruit size when compared to 'DrisRaspTwelve'. Further, for 'DrisRaspEighteen' the leaves have predominantly three leaflets, the profile of leaflets in cross section is straight, and the leaf rugosity is weak, whereas for 'DrisRaspTwelve' the leaves have equally three and five leaflets, the profile of leaflets in cross section is concave, and the leaf rugosity is medium.

'DrisRaspEighteen' differs from the male parent 'DrisRaspThirteen' (U.S. Plant Pat. No. 29,402) in that 'DrisRaspEighteen' has an improved flavor and higher yield when compared to 'DrisRaspThirteen'. Further, for 'DrisRaspEighteen' the bloom on current season's cane is absent or very sparse, the density of spines is sparse, and the fruit glossiness is strong, whereas for 'DrisRaspThirteen' the bloom on current season's cane is medium, the density of spines is medium, and the fruit glossiness is medium.

'DrisRaspEighteen' differs from reference raspberry variety 'Driscoll Maravilla' (U.S. Plant Pat. No. 14,804) in that for 'DrisRaspEighteen' the leaves have predominantly three leaflets, the relative position of the lateral leaflets is free, the fruit's adherence to the plug is weak, and the leaf rugosity is weak, whereas for 'Driscoll Maravilla' the leaves have predominantly five leaflets, the relative position of the lateral leaflets is overlapping, the fruit's adherence to the plug is medium, and the leaf rugosity is medium.

'DrisRaspEighteen' differs from reference raspberry variety 'DrisRaspSeven' (U.S. Plant Pat. No. 25,045) in that for 'DrisRaspEighteen' the bloom on current season's cane is absent or very weak, the predominant number of leaflets on leaves is three, the number of spines on the pedicel is few, and the fruit firmness is firm, whereas for 'DrisRaspSeven' the bloom on current season's cane is medium, the predominant number of leaflets on leaves is five, the number of spines on the pedicel is absent or very few, and the fruit firmness is medium.

What is claimed is:

1. A new and distinct variety of raspberry plant designated 'DrisRaspEighteen' as shown and described herein.

* * * * *